United States Patent
Lin

(10) Patent No.: US 10,407,684 B2
(45) Date of Patent: Sep. 10, 2019

(54) **METHOD FOR DIRECT TRANSFORMATION OF EXOGENOUS DNA INTO RESTING SPORES OF *ASPERGILLUS NIGER* INDEPENDENT OF MEDIATORS**

(71) Applicant: FuZhou University, Fujian (CN)

(72) Inventor: Jun Lin, Fujian (CN)

(73) Assignee: FuZhou University, Fujian (CN)

( * ) Notice: Subject to any disclaimer, the term of this patent is extended or adjusted under 35 U.S.C. 154(b) by 0 days.

(21) Appl. No.: 16/076,698

(22) PCT Filed: Oct. 21, 2016

(86) PCT No.: PCT/CN2016/102926
§ 371 (c)(1),
(2) Date: Aug. 9, 2018

(87) PCT Pub. No.: WO2018/045618
PCT Pub. Date: Mar. 15, 2018

(65) Prior Publication Data
US 2019/0048355 A1    Feb. 14, 2019

(30) Foreign Application Priority Data

Sep. 9, 2016 (CN) .......................... 2016 1 0813630

(51) Int. Cl.
| *C12N 15/80* | (2006.01) |
| *A61K 38/16* | (2006.01) |
| *C12R 1/66* | (2006.01) |

(52) U.S. Cl.
CPC .............. *C12N 15/80* (2013.01); *A61K 38/16* (2013.01); *C12R 1/66* (2013.01)

(58) Field of Classification Search
CPC .... A61K 38/16; A61K 38/08; A61K 41/0009; A61K 41/0057; A61K 41/0071; A61K 47/10; A61K 47/26; A61K 47/34; A61K 47/64; A61K 47/6911; A61K 8/64; A61K 9/0019; A61K 9/0063; A61K 9/06; A61K 38/00; A61K 38/168; A61K 38/17; A61K 9/0053; A61K 38/164; A61K 38/1703; A61K 38/1709; A61K 38/1767; A61K 38/38; A61K 38/45; A61K 45/06; A61K 9/0075; A61K 9/0095; A61K 9/146; A61K 9/2054; A61K 9/2866; A61K 38/56; A61K 39/523; A61K 2039/552; A61K 39/00; A61K 39/0208; A61K 39/07; A61K 8/66
See application file for complete search history.

(56) References Cited

U.S. PATENT DOCUMENTS

2005/0070007 A1    3/2005  Romaine et al.

FOREIGN PATENT DOCUMENTS

| CN | 101544986 | 9/2009 |
| CN | 1995362   | 6/2010 |

OTHER PUBLICATIONS

"International Search Report (Form PCT/ISA/210)", dated Jun. 7, 2017, with English translation thereof, pp. 1-4.
Ozeki et al, "Transformation of intact Aspergillus niger by electroporation," Biosci. Biotech. Biochem., Dec. 1994, pp. 2224-2227.
Storms et al, "Plasmid vectors for protein production, gene expression and molecular manipulations in Aspergillus niger," Plasmid, Nov. 2004, pp. 191-204.
Wu et al, "High-density distributed electrode network, a multifunctional electroporation method for delivery of molecules of different sizes," Scientific reports, Nov. 28, 2013, pp. 1-7.

*Primary Examiner* — Padmavathi Baskar
(74) *Attorney, Agent, or Firm* — JCIPRNET

(57) ABSTRACT

The present invention discloses a method for direct transformation of exogenous DNA into resting spores of *Aspergillus niger* independent of mediators. The method includes three steps of culture of *Aspergillus niger* and collection of spores, pretreatment of *Aspergillus niger* spores, and electroporation of *Aspergillus niger* spores by using HDEN method, to obtain *Aspergillus niger* spores with introduction of plasmids to be transformed. In the present invention, non-germinated spores are used as a starting material for introduction of an exogenous molecule, and exogenous DNA is introduced into the resting spores of *Aspergillus niger* by employing the HDEN electrotransformation technique, whereby the complex step of spore germination is omitted, and steps of protoplast preparation or *Agrobacterium*-mediated transformation in conventional methods etc. are omitted. Moreover, the transformation efficiency is high, and at least an effect of no less than 6000 positive transformants per transformation reaction system can be achieved.

10 Claims, 1 Drawing Sheet
Specification includes a Sequence Listing.

MET
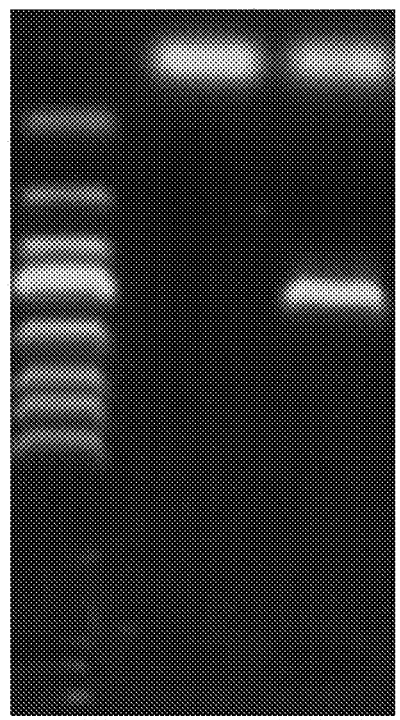
marker   1      2

METHOD FOR DIRECT TRANSFORMATION OF EXOGENOUS DNA INTO RESTING SPORES OF ASPERGILLUS NIGER INDEPENDENT OF MEDIATORS

CROSS-REFERENCE TO RELATED APPLICATION

This application is a 371 application of an international PCT application serial no. PCT/CN2016/102926, filed on Oct. 21, 2016, which claims priority to and the benefit of China Patent Application No. 201610813630.X, filed on Sep. 9, 2016. The entirety of each of the above-mentioned patent applications is hereby incorporated by reference herein and made a part of this specification.

BACKGROUND OF THE INVENTION

1. Field of the Invention

The present invention relates to the field of biological technologies, and specifically to a method for direct transformation of exogenous DNA into resting spores of *Aspergillus niger* independent of mediators.

2. Description of Related Art

*Aspergillus niger* is a eukaryotic microorganism and a filamentous fungus. *Aspergillus niger* is an important strain in fermentation industry, with which a variety of important industrial products such as amylase, acid protease, cellulase, pectinase, glucose oxidase, citric acid, gluconic acid and gallic acid can be produced. *Aspergillus niger* is a microbial species classified as GRAS (Generally Recognized as Safe) certified by the United States Food and Drug Administration. It is generally accepted in the field that the application of GRAS is substantially not harmful to human and the environment, and therefore, these microbial strains are able to meet a variety of increasingly stringent and harsh quality standards and can easily pass a variety of biosafety and food safety approval processes. Accordingly, the importance of *Aspergillus niger* in the modern fermentation industry is evident.

With molecular genetics as a theoretical basis, and by means of modern methods of molecular biology, genetic engineering aims at changing the original genetic characteristics of organisms to obtain new varieties and produce new products by constructing a DNA molecule in vitro with genes of different sources according to a pre-designed blueprint followed by transformation into cells. (For example, an enzyme gene with important economic value is transformed into *Aspergillus niger* cells for high expression of the enzyme protein, thereby producing the enzyme.) In this area, a very important part is introduction of foreign DNA into cells. For different species and different states of the cells, different transformation methods are needed, to enable the foreign DNA to cross the cell wall and the cell membrane, transporting into the cells.

At present, the main DNA transformation methods for use in the field of filamentous fungi (including *Aspergillus niger*) includes:

1. Protoplast-mediated transformation: in this method, various enzymes are used to hydrolyze the cell wall of fungal mycelia, to expose the cell membrane, under certain chemical conditions, the cell membrane can absorb exogenous DNA. However, since the structure and composition of the fungal cell wall are complex, and the structures and compositions of the cell walls of different species and even different subspecies of the same species are different, hence the methods of protoplast preparation cannot be unified. Moreover, for many fungi, especially *Aspergillus niger*, the protoplast preparation is very difficult, the steps are extremely cumbersome, and special, expensive cell wall hydrolases are required.

2. *Agrobacterium tumefaciens*-mediated transformation: *Agrobacterium tumefaciens* is a Gram-negative bacterium that infects plant callus and filamentous fungi, and able to insert the circular plasmid Ti-DNA which is stably inherited in cells into the host genome. However, the method has cumbersome steps, and is time-consuming; and *Agrobacterium tumefaciens* has selectivity to hosts, so this method is not suitable for all the fungi. In addition, the location at which the exogenous DNA is inserted into the host genome is random and unpredictable. The exogenous DNA can only be inserted into the host genome and unable to sustain adrift in the host cytoplasm.

3. Biolistic transformation: in this method, DNA is adsorbed on the surface of special metal particles, using gunpowder explosion or a high-pressure gas acceleration, the metal particles adsorbed with DNA are directly introduced into intact tissues or cells. This method requires very expensive special laboratory equipment, and the metal particles used in the consumables often require to use gold materials. In addition, transformation efficiency of this method is not high, the host cells have a high death rate under the bombardment of metal particles, and regeneration is difficult, hence the scope of use is limited.

4. Electroporation: this is a method using short electrical pulse on cells exposed to exogenous DNA, causing exogeneous DNA to enter the cells, thereby changing the genetic characteristics of the cells. Unlike the *Agrobacterium*-mediated transformation that requires *Agrobacterium* as a mediator and the biolistic transformation that requires metal particles as a mediator, this method does not require a mediator to carry the exogenous DNA. The traditional electroporation includes exponential decay wave electroporation and square wave electroporation. The energy for exponential decay wave electroporation is particularly high, causes big damage to the cells. Due to microbial cells have simple structure, presence of cell wall, strong cell resistance, high vitality, and many microbial cells have hard shells, they can withstand high-energy electroporation, hence the exponential decay wave electroporation is generally only for microbial cells. However, mammalian cells (such as human cell lines) are relatively fragile and prone to death compared to microbes. Therefore, the square wave electroporation is commonly used in mammalian cells. In addition, the square wave electroporation is also widely used for in-vivo electroporation in small animals such as mice.

High-density distributed electrode network (HDEN) electrotransformation technique introduced in 2013 is an electrotransformation technique developed specifically for the characteristics of mammalian cells, with the purpose of to improve the efficiency of delivery of exogenous DNA and drug to mammalian cells. The technique consists of three parts, first is the form of an electric pulse applied to cell sample, second is the solution environment where the cell sample is electroporated, and third is the culturing method of the cell sample and the pre-treatment method before electroporation. Because the technique is developed specifically for mammalian cells, the above-mentioned three parts are designed targeted for the characteristics of mammalian cells.

It is well known in the art that the characteristics and the culturing method of microbial cells are vastly different from those of mammalian cells. The structures of mammalian cells and microbial cells are different. Mammalian cells have no cell walls. Microbial cells (such as most fungi, including *Aspergillus niger*) have cell walls. The cell membrane of mammalian cells is also different from the cell membrane of microbial cells.

Therefore, any technique applied to mammalian cells is difficult to be directly applied to microbial cells. Application of the HDEN technique in mammalian cells such as HEK-293A, Hela, Neuro-2A, MCF-7, C2C12, 3T3-L1, CHO, MDCK, HL-60, HUVEC, A375, U251 etc. is reported in current literatures. Currently, there is no reports on the use of this technique in species other than mammalian cells at present. Therefore, whether the HDEN electrotransformation technique can be applied to species other than mammalian cells is still unknown.

Filamentous fungi (including *Aspergillus niger*) are a class of eukaryotic microorganisms, and the genomes of many types of fungi are polyploid. The most difficult problem encountered when performing genetic engineering to a living organism is polyploidy. Because engineering on polyploid is often inefficient (for example, gene targeting may hit only one chromosome, and be off target to the other one or several homologous chromosomes), and during cell division in reproduction of a polyploid, homologous chromosomes are segregated, and the engineered site is difficult to pass on to all the progenies. This is well known in the art.

Fungal spores are the major reproductive organs of fungi, and the spores are dormant and can survive for a long time. Spores are activated and germinated under appropriate external conditions, to form mycelia for split propagation. Most importantly, the spores of many types of fungi are native haploids. Haploid can be genetically engineered directly and the efficiency is much higher than manipulating polyploids.

However, since the spores are generally dormant, their cell walls are very thick, and the state of the cell wall and cell membrane of resting spores are different from those of germinated spores and mycelia. Moreover, the intracellular life activity of resting spores is also in the least exuberant state. Therefore, it is well known in the art that resting spores have less cell permeability compared to germinated spores and mycelia. The resting spores hardly exchange substance with the exterior, and is inactive and is generally in dormant state. However, the germinated spores or mycelia, require uptake of nutrients from the exterior for life activities, so permeability of the cell wall and cell membrane is higher than the resting spores. Therefore, it is very difficult to introduce exogenous DNA molecules directly into the interior of sleeping spores.

For the several available well-established techniques, in the protoplast-mediated transformation, the source of protoplasts in the host cells, is generally the mycelia body of fungi (polyploid). In the *Agrobacterium*-mediated transformation, *Agrobacterium* and fungal spores are co-cultured on the surface of a solid culture medium for several days, exogenous DNA can be introduced into fungal cells, under the mediation of *Agrobacterium*. However, this is not a direct transformation of spores, because fungal spores germinate during co-cultivation and subsequently *Agrobacterium* invades the germinated spores to introduce the exogenous DNA. Moreover, in the *Agrobacterium*-mediated transformation, *Agrobacterium* is needed as a mediator, and transformation of *Agrobacterium* has to be carried out before subsequent fungal transformation, hence the operation is very complicated and cumbersome, and the cycle is long.

In the conventional electroporation method (using exponentially decay wave electroporation), the host cells used are germinated fungal spores. For example, in the method developed by Ozeki et al., the spores have to be germinated first and electroporation can be performed subsequently (specific experimental steps and details for spore germination are disclosed in the method). This method is a pioneer to typical techniques in the field, so far there is no significant improvement, and the method is in use in the field until now. Inventors of the present application attempted to transform non-germinated spores by using this method, and it was unsuccessful. So far, there is no successful reports in the literatures. The method developed by Ozeki et al. is described in literature 1: OZEKI K, KYOYA F, HIZUME K, KANDA A, HAMACHI M, NUNOKAWA Y. Transfoiniation of intact *Aspergillus niger* by electroporation [J]. Biosci Biotechnol Biochem, 1994, 58(12): 2224-2227.

At present, there is no method or any report, that is able to introduce exogenous DNA molecule directly into resting (non-germinated) fungal spores in the absence of a mediator. This is also a technical problem that has not been overcome in the art.

SUMMARY OF THE INVENTION

In view of the existing defects in the art, an objective of the present invention is to provide a method for direct transformation of exogenous DNA into resting spores of *Aspergillus niger* independent of mediators, in which the step of fungal spore germination is bypassed, and the exogenous DNA is directly introduced into resting spores by using HDEN electrotransformation technique.

To achieve the above objective, the present invention employs the following technical solutions:

A method for direct transformation of exogenous DNA into resting spores of *Aspergillus niger* independent of mediators includes the steps of:

1) Culture of *Aspergillus niger* and Collection of Spores

*Aspergillus niger* is inoculated onto a surface of a solid agar medium, and cultured until the *Aspergillus niger* spores are overgrown on the surface of the medium, the *Aspergillus niger* spores are washed off from the surface of the medium, suspension of the spores is aspirated off and filtered to remove mycelia, and filtrate containing the spores is collected, and centrifuged to collect the pelleted resting spores;

2) Pretreatment of *Aspergillus niger* Spores the spores are re-suspended in an electroporation buffer, and centrifuged to collect the spore pellets, the re-suspension and centrifugation steps are repeated 3-4 times, and the last collected spore pellets are re-suspended in the electroporation buffer, to obtain an *Aspergillus niger* spore suspension with a spore concentration of $10^4$-$10^{11}$ spores/ml, in which the electroporation buffer consists of 4-hydroxyethyl piperazine ethanesulfonic acid (HEPES) having a final concentration of 0.01-100 mmol/L and mannitol having a final concentration of 0.5-5000 mmol/L, and the pH of the electroporation buffer is 3.0-9.5; and 3) Electroporation of *Aspergillus niger* Spores by Using HDEN Method the *Aspergillus niger* spore suspension prepared in the above steps and a plasmid to be transformed are added to wells of a cell culture plate and mixed uniformly, to obtain a mixture of the spores and the plasmid, the cell culture plate is placed on an ice bath for 10-15 min, electroporation is carried out subsequently by using the HDEN method using an Etta Biotech X-Porator H1 electroporator, by inserting an electroporator head fitted with a matrix electrode into the mixture of the spores and the plasmid, and energizing, to generate an electric field inside the mixture of the spores and the plasmid, the cell culture plate is placed on the ice bath again for 10-15 min after electroporation, and subsequently the mixture of the spores and the plasmid is aspirated off, to obtain resting spores of *Aspergillus niger* with introduction of exogenous DNA, in which ratio of the *Aspergillus niger* spore suspension to the plasmid to be transformed is 6-600000 μl of *Aspergillus niger* spore suspension to 0.1-10000 μg of plasmid to be transformed; and parameters for the electroporation include: a voltage of 1-6000 V, pulse duration of 2-2000000 ms, and repeat for 1-100 times at an interval of 5-50000 ms.

Further, the medium in the step 1) is PDA medium, YPD medium or Czapek-Dox medium, and the preferable PDA medium is with the best outcome and the spore production capability is the fastest and the largest.

In the step 1), *Aspergillus niger* is at a temperature of 16-40° C. with 15-85% humidity for 3-15 days.

Preferably, in the step 1), *Aspergillus niger* is cultured at a temperature of 30° C. with 50-60% humidity for 5 days.

Further, in the step 2), the electroporation buffer consists of HEPES having a final concentration of 1-10 mmol/L and mannitol having a final concentration of 50-100 mmol/L, and the pH of the electroporation buffer was 5.0-7.0.

Preferably, in the step 2), the electroporation buffer consists of HEPES having a final concentration of 1 mmol/L and mannitol having a final concentration of 50 mmol/L, and the pH of the electroporation buffer was 7.0.

In the step 2), the *Aspergillus niger* spore suspension is observed under a microscope before electroporation, to confirm that the spore suspension is free of contamination with mycelia and the spores are non-germinated, and subsequently electroporation is carried out.

Further, in the step 3), the plasmid to be transformed is recombinant plasmid AnEp8-hygro, and the recombinant plasmid AnEp8-hygro is constructed with a hygromycin B resistance gene and an AnEp8 plasmid, and the electroporation is carried out by using the Etta Biotech X-Porator H1 electroporator.

Preferably, the ratio of the *Aspergillus niger* spore suspension to the recombinant plasmid AnEp8-hygro is 60 μl of *Aspergillus niger* spore suspension to 1 μg of recombinant plasmid AnEp8-hygro.

Further, in the step 3), the voltage is 400-3000 V, the pulse duration is 200-1000000 ms, repeat for 2-52 times at an interval of 500-5000 ms. Preferably, the voltage is 400 V, the pulse duration is 2000 ins, repeat for 3 times at an interval of 500 ms.

Further, to confirm that the exogenous DNA has been introduced into resting spores of *Aspergillus niger*, the step 3) further includes, after electroporating and further standing on an ice bath, aspirating the mixture of the spores and the plasmid off, coating the mixture onto a plate containing YPD solid agar medium with a final concentration of hygromycin B of 200 μg/ml, culturing the mixture at 16-40° C. and preferably 28° C. with 15-85% humidity and preferably 50-60% humidity until single colonies are formed, and counting the colonies.

The hygromycin B (CAS number: 31282-04-9) is dissolved in sterilized high-purity water, to prepare a stock of high concentration, which is diluted in medium according to a desired ratio before use.

At the same time when the above experimental steps are performed, a control group needs to be prepared. The same mixture of "the spores and the plasmid" that is not electroporated is coated onto another plate containing YPD solid agar medium with a final concentration of hygromycin B of 200 μg/ml, and cultured under the same conditions. No single colony is formed in the control group, and the single colonies in the experimental group are determined to be positive clones.

When single colonies are forged in the experimental group, DNA is extracted from the single colonies in the experimental group, and the exogenous hygromycin B resistance gene which may contained in the DNA is amplified by PCR. The band size of the amplified product is determined by agarose gel electrophoresis. When the band size is as expected, the amplified product is subjected to Sanger DNA sequencing to determine if its DNA sequence is consistent with that of the exogenous hygromycin B resistance gene. If consistent, it can be accurately determined that the positive clones are successful transformants.

The *Aspergillus niger* mentioned in the present invention is *Aspergillus niger* CBS 513.88, and the electroporation is carried out by using the Etta Biotech X-Porator H1 electroporator purchased from Suzhou Etta Biotech Co., Ltd.

In the present invention, the experimental operations of collection of non-germinated spores and the subsequent electroporation process are all conducted in the laboratory at a constant temperature not higher than 23 degrees Celsius; the centrifugation steps are all 4° C. cold centrifugation; and various kinds of liquid exposed to the non-germinating spores are all pre-cooled on ice in advance, unless otherwise indicated. The non-germinated spores are prohibited from contacting any factors and substances which are able to promote their germination (such as YEPD, etc. as a representative medium for germination), to ensure the dormancy of spores.

During the culture process of *Aspergillus niger* in the present invention, when *Aspergillus niger* spores are overgrown on the surface (where the spores appear dark brown), sterilized water was poured onto the surface of the medium, to wash the *Aspergillus niger* spores off from the surface of the medium. The spore suspension is aspirated with a pipette and filtered using sterilized lens paper (or fitted glass filter, filter paper, etc.) to remove the mycelia and retain the spores. If there is no filtration step, the spore suspension will be mixed up with mycelia, and it is unable to determine whether the transformants obtained in the subsequent steps are positive clones formed after transformation of DNA into the spores, or false positive clones formed after the transformation of DNA into the mycelia. The resulting spores are subjected to chromosome staining, to observe and confirm that the chromosomes in the spores are haploid.

The water used to prepare the solid agar medium in the present invention should be Milli-Q-grade high-purity water or double distilled water having a resistivity of not lower than 18.2 MΩ·cm used in molecular biology.

When *Aspergillus niger* spores are electroporated by using the HDEN method, the *Aspergillus niger* spore suspension and the plasmid to be transformed are added at a proper ratio to the wells of a cell culture plate and mixed evenly. The cell culture plate was placed on an ice bath. For example, in a well of a 96-well cell culture plate (Nunclon Surface 96-well cell culture plate from NUNC, Cat. No. 167008), 60 μl of the *Aspergillus niger* spore suspension and 1 μg of the recombinant plasmid AnEp8-hygro are added. The cell culture plate can also be a 384-well plate, a 24-well plate, a 6-well plate, or other larger or smaller containers, and subsequently the mixture system of the spore and the plasmid can be enlarged or reduced according to the volume size ratio of the containers.

In the present invention, the above technical solution is employed. It is very simple to use non-germinated spores as a starting material for introducing exogenous molecules because the complicated step of germination of spores can be omitted. More importantly, polyploidy might have occurred in the germinated spores, whereas non-germinated spores are guaranteed to be haploid. In many applications of genetic engineering, the host cells have to be haploid in order to achieve the desired result or efficiency. Meanwhile, the HDEN electrotransformation technique is utilized in the present invention to introduce exogenous DNA into resting spores of *Aspergillus niger*. In the HDEN electrotransformation technique, a high-density matrix electrode that produces a highly uniform and intense electric field is used. Each cell within the electric field receives an electroporation condition which is almost exactly the same. During operation, the cells are placed in a common container, such as a cell culture plate, and followed by inserting an electroporator head with a matrix electrode into the container, and energized. In the traditional electroporation technique, a special electroporation cuvette is generally used, cells are placed between two metal plates positioned in parallel and subsequently the metal plates are electrified to form an electric field for electroporation. Therefore, the discharge modes in the two methods are completely different. In the former one, the electrode is inserted into the cell suspension and an electric field is generated within, whereas in the latter one, an electric field is generated outside of the whole cell suspension. In the former one, the electrode head is formed by many metal pins, and a voltage is generated between the pins, whereas in the latter one, only two metal plates are present, i.e. a positive electrode plate and a negative electrode plate, and a voltage is generated between the two plates. The HDEN technique also basically eliminates the cathode effect existing in the traditional electroporation technology, to avoid the generation of large amounts of hydroxide ions, so as to avoid killing the cells and improve the cell survival rate after electroporation. However, the cathode effect is difficult to be eliminated in the traditional electroporation technology. Further, in traditional electroporation methods, the electroporation is performed only once. This is because if multiple electroporations are performed, the cell death rate will be increased greatly. However, in the HDEN method of the present invention, multiple electroporations may be performed, and the effects of the multiple electroporations can be superimposed without significantly increasing the cell death rate.

The HDEN electrotransformation technique is an electrotransformation technique developed specifically for the characteristics of mammalian cells, to improve the efficiency of delivery of exogenous DNA and drug to mammalian cells. It is well known in the art that the characteristics and the culturing method of microbial cells are vastly different from those of mammalian cells. The structures of mammalian cells and microbial cells are different. Mammalian cells have no cell walls. Microbial cells (such as most fungi, including *Aspergillus niger*) have cell walls. The cell membrane mammalian cells is also different from the cell membrane of microbial cells. Even in case of the same organism, the structures, states, and chemical compositions of respective cell membrane and cell wall of different tissues, different organs or different cell types are also different. Even the structures, states, and chemical compositions of respective cell membrane and cell wall of the same tissue, the same organ, and the same cell type of the same organism are also different in different stages of growth and development or in different external environments. The cell wall and cell membrane are barriers that block exogenous molecules to enter the cell. Depending on different barriers (with different structures and different chemical compositions), the methods to break through the barriers are different. In addition, different exogenous molecules when encountering the same barrier, because of their different structures, molecular weights, volumes and chemical compositions, the methods by which these different exogenous molecules break through the barrier are also different. If encounter with different barriers, the methods and mechanisms by which different exogenous molecules break through the different barriers are even vastly different.

Therefore, any technique applied to mammalian cells is difficult to be applied directly to microbial cells. There are no reports of the use of HDEN technique in species other than mammalian cells at present. In the present invention, the exogenous DNA is introduced into resting spores of *Aspergillus niger* by using the HDEN technique according to the characteristics of *Aspergillus niger* cells. In the method, the culture method of the cell sample, the pre-treatment method before electroporation, the solution environment of the cell sample during the electroporation, and the form of an electric pulse applied on the cell sample are determined. Employing the method of the present invention is very simple and rapid, in which the wild spores can be directly used as a raw material, preparing the spores in the competent state is not required, and removing the cell wall of the spores by various cumbersome methods (e.g. enzymatic hydrolysis) is not required. The method just requires washing the wild spores and re-suspending them in the electroporation buffer, in which the steps are very simple. In the conventional protoplast-mediated transformation, a special cell wall hydrolase, and complex steps of preparing and regenerating protoplast are required. In the conventional electroporation, spores required germination treatment prior to use, electroporation is performed after the spores are germinated, and the transformation efficiency is low. In the conventional *Agrobacterium*-mediated transformation, *Agrobacterium* is transformed first and followed by subsequent transformation of *Aspergillus niger*. In the conventional biolistic transformation, it requires expensive consumables, and the transformation efficiency is low.

Ozeki et al. reported the transformation efficiency of germinated spores of *Aspergillus niger* by conventional exponential decay wave electroporation method and the transformation efficiency of *Aspergillus niger* using the protoplast-mediated method. The protoplast-mediated method is preferred, with a transformation efficiency of no more than 500 transformants/μg plasmid and requiring $10^7$ host cells.

The transformation efficiency of the method in the present invention is high, and at least an effect of no less than 6000 positive transformants per transformation reaction system is achieved. For example, the size of the AnEp8-hygro plasmid used in Example 1 is 12.4 kb. Using 1 μg of plasmid (about 124.26 fmol plasmid molecules), electroporation of $6 \times 10^6$ non-germinated resting spores of *Aspergillus niger* results in no less than 8000 positive transformants.

It is well known that the plasmid size is inversely proportional to the transformation efficiency. The larger the plasmid size, the more difficult to penetrate cross the cell wall and cell membrane. The 12.4 kb plasmid used in the present invention is a very large plasmid. It is reported in the literature that the size of the plasmids used in most of the transformation of *Aspergillus niger* (protoplast-mediated transformation, and electroporation) is less than 8 kb.

Currently there are various methods describing on transformation efficiency, including the number of positive transformants produced by a given μg of plasmids; the number of positive transformants produced by a given number of plasmids (number of moles, number of DNA molecules); and the number of positive transformants produced by a given number of host cells, etc. In the present invention, various indicators of number of host cells, plasmid quality, plasmid number and plasmid molecular weight etc. are disclosed. The transformation efficiency of a transformation system evaluated in any way can be calculated and converted by means of the indicators disclosed in the present invention.

BRIEF DESCRIPTION OF THE DRAWINGS

FIG. 1 is an agarose gel electrophoresis to confirm whether a sample contains the hygromycin resistance gene after PCR amplification in Example 1.

DESCRIPTION OF THE EMBODIMENTS

The following examples are provided for a better understanding of the present invention; however, the present invention is not limited thereto.

All the experimental process should follow the principle of aseptic condition while conducting the microbial experiments, and the instruments, consumable materials, and reagents should be sterilized.

Example 1

A method for direct transformation of exogenous DNA into resting spores of *Aspergillus niger* independent of mediators includes the following steps:

1) Culture of *Aspergillus niger* and Collection of Spores

In a 15-cm Petri dish, a solid agar medium (PDA medium) was prepared. *Aspergillus niger* CBS 513.88 was inoculated onto the surface of the solid agar medium and cultured at a temperature of 30° C. with 50-60% humidity for 5 days, to allow *Aspergillus niger* spores to overgrow on the surface of the medium (where the spores appeared dark brown and was easy to visually identified).

Sterilized water was poured onto the surface of the medium, to wash down the *Aspergillus niger* spores off from the surface of the medium (by vibrating, or gently scratching with a sterilized smooth glass spreading rod). The spore suspension was aspirated with a pipette and filtered using sterilized lens paper (or fitted glass filter, filter paper, etc.) to remove the mycelia and retain the spores. The filtered liquid was placed in a centrifuge tube and centrifuged to collect the pelleted resting spores, and the supernatant was discarded. The collected spores were subjected to chromosome staining, to observe and confirm that the chromosomes in the spores are haploid.

2) Pretreatment of *Aspergillus niger* Spores

The spore pellets were re-suspended in an electroporation buffer (where the volume of the electroporation buffer added should fill up the centrifuge tube), centrifuged again to collect the spore pellets, and the supernatant was discarded. After repeating the above steps twice, the spores were re-suspended in the electroporation buffer again, and observed under a microscope, to confirm that the spore suspension was free of contamination with mycelia and the spores were non-germinated. When the spores were finally re-suspended in the electroporation buffer, the volume of the electroporation buffer was controlled to maintain a spore concentration in the *Aspergillus niger* spore suspension of $10^8$ spores/ml.

The electroporation buffer consisted of HEPES having a final concentration of 1 mmol/L and mannitol having a final concentration of 50 mmol/L, and the pH of the electroporation buffer was 7.0.

3) Electroporation of the *Aspergillus niger* Spores by Using HDEN Method

60 μl of the *Aspergillus niger* spore suspension and 1 μg of recombinant plasmid AnEp8-hygro were added to wells of a 96-well cell culture plate and mixed evenly, to obtain a mixture of the spores and the plasmid. The cell culture plate was placed on an ice bath for 10 min, electroporation was carried out subsequently by using the HDEN method using an Etta Biotech X-Porator H1 electroporator, by inserting an electroporator head fitted with a matrix electrode into the mixture of the spores and the plasmid, and energizing, to generate an electric field inside the mixture of the spores and the plasmid. The cell culture plate was placed on the ice bath again for 10 min after electroporation, and subsequently the mixture of the spores and the plasmid was aspirated off, to obtain resting spores of *Aspergillus niger* with introduction of exogenous DNA.

In this example, the parameters for electroporation include: a voltage of 400 V, pulse duration of 2000 ms, and repeat for 3 times at an interval of 500 ms.

4) Confirmatory Experiment

The aspirated mixture of the spores and the plasmid was coated onto a plate containing YPD solid agar medium with a final concentration of hygromycin B of 200 μg/ml, and cultured at a temperature of 28° C. with 50-60% humidity until single colonies were formed. The colonies were counted and the transformation efficiency was calculated.

At the same time when the above experimental steps were performed, a control group was prepared. The same mixture of "the spores and the plasmid" that was not electroporated was coated onto another plate containing YPD solid agar medium with a final concentration of hygromycin B of 200 μg/ml, and cultured under the same conditions. No single colony was formed in the control group, and the single colonies in the experimental group were determined to be positive clones.

When single colonies were formed in the experimental group, DNA was extracted from the single colonies in the experimental group, and the exogenous hygromycin B resistance gene which may contained in the DNA was amplified by PCR. The band size of the amplified product was determined by agarose gel electrophoresis. The result of electrophoresis is shown in FIG. 1. The direction of electrophoresis is from bottom to top. The Marker is Takara 250 bp DNA ladder marker, lane 1 is negative control, and a clear band is observed at about 1 kb in lane 2, which is consistent with the band of hygromycin B resistance gene, indicating successful transformation. That is to say the lane 2 is the band of the amplified hygromycin B resistance gene. Sanger DNA sequencing result shows that the DNA sequence is consistent with the exogenous hygromycin B resistance gene, hence it can be accurately determined that the positive clone in this example is a successful transformant.

The volume of the AnEp8-hygro plasmid in this example was 12.4 kb, and 1 plasmid (about 124.26 fmol plasmid molecules) was used, with which $6 \times 10^6$ non-germinated resting spores of *Aspergillus niger* were electroporated, to produce no less than 8000 positive transformants.

The recombinant plasmid AnEp8-hygro in this example was constructed with a hygromycin B resistance gene and an AnEp8 plasmid. The construction of the recombinant plasmid AnEp8-hygro was as follows:

The hygromycin B resistance gene is as shown in SEQ ID NO. 1.

The protein sequence encoded is as shown in SEQ ID NO. 2.

The hygromycin B resistance gene was amplified by PCR using primers:

```
F:
                                            (SEQ ID NO. 4)
CATTAGCTAGCATGAAAAAGCCTGAACTCACCG

R:
                                            (SEQ ID NO. 5)
TCTGGCGCGCCCTATTCCTTTGCCCTCGG
```

PCR system (50 μL): template 3 μL, primer F (10 μM) 2 μL, primer R (10 μM) 2 μL, 2× Taq PCR mix 25 μL, and ddH$_2$O top up to 50 μL.

PCR program: 94° C. for 10 min, 35 cycles of (94° C. for 30 s, 61.8° C. for 30 s, and 72° C. for 90 s), and 72° C. for 10 min.

The PCR product was confirmed by agarose gel electrophoresis, and after correct detection, the PCR product was recovered by using Thermo GeneJET Gel Extraction and DNA Cleanup Micro Kit.

The AnEp8 plasmid was a gift from U.S. Fungal Genetics Stock Center (FGSC), and was described in literature 2: STORMS R, ZHENG Y, LI H, SILLAOTS S, MARTINEZ-PEREZ A, TSANG A. Plasmid vectors for protein production, gene expression and molecular manipulations in *Aspergillus niger* [J]. Plasmid, 2005, 53(3): 191-204.

The AnEp8 plasmid in the literature 2 was used. The AnEp8 plasmid has a sequence as shown in SEQ ID NO. 3. The AnEp8 plasmid was extracted using plasmid extraction kit available from Shanghai Sangon Biotech. The AnEp8 plasmid and purified PCR product of hygromycin B resistance gene were double-digested by Fastdigest restriction endonucleases NheI and AscI from Fermentas, subjected to agarose gel electrophoresis, and extracted (by using Thermo GeneJET Gel Extraction and DNA Cleanup Micro Kit). The hygromycin B gene was ligated to the AnEp8 plasmid by using T4 DNA ligase (product of Fermentas). The enzymatic cleavage and ligation operations were carried out strictly according to manufacturer's instruction. Subsequently, *Escherichia coli* transformation was performed, to construct a recombinant plasmid Anep8-hygro. The recombinant plasmid Anep8-hygro was subjected to Sanger sequencing and after confirmed by double-digestion, the *Escherichia coli* cells were mass cultured, and the recombinant plasmid was extracted by using a plasmid extraction kit (EndoFree Plasmid Maxi Kit) from Qiagen (according to manufacturer's instruction).

Example 2

A method for direct transformation of exogenous DNA into resting spores of *Aspergillus niger* independent of mediators includes the following steps:

1) Culture of *Aspergillus niger* and Collection of Spores

In a 15-cm Petri dish, a solid agar medium (YPD medium) was prepared. *Aspergillus niger* CBS 513.88 was inoculated onto the surface of the solid agar medium and cultured at a temperature of 16° C. with 15-50% humidity for 15 days, to allow *Aspergillus niger* spores to overgrow on the surface of the medium (where the spores appeared dark brown and was easy to visually identified).

Sterilized water was poured onto the surface of the medium, to wash down the *Aspergillus niger* spores off from the surface of the medium (by vibrating, or gently scratching with a sterilized smooth glass spreading rod). The spore suspension was aspirated with a pipette and filtered using sterilized lens paper (or fritted glass filter, filter paper, etc.) to remove the mycelia and retain the spores. The filtered liquid was placed in a centrifuge tube and centrifuged to collect the pelleted resting spores, and the supernatant was discarded. The collected spores were subjected to chromosome staining, to observe and confirm that the chromosomes in the spores are haploid.

2) Pretreatment of *Aspergillus niger* Spores

The spore pellets were re-suspended in an electroporation buffer (where the volume of the electroporation buffer added should fill up the centrifuge tube), centrifuged again to collect the spore pellets, and the supernatant was discarded. After repeating the above steps twice, the spores were re-suspended in the electroporation buffer again, and observed under a microscope, to confirm that the spore suspension was free of contamination with mycelia and the spores were non-germinated. When the spores were finally re-suspended in the electroporation buffer, the volume of the electroporation buffer was controlled to maintain a spore concentration in the *Aspergillus niger* spore suspension of 10" spores/ml.

The electroporation buffer consisted of HEPES having a final concentration of 0.01 mmol/L and mannitol having a final concentration of 0.5 mmol/L, and the pH of the electroporation buffer was 3.0.

3) Electroporation of the *Aspergillus niger* Spores by Using HDEN Method

6 μl of the *Aspergillus niger* spore suspension and 0.1 μg of recombinant plasmid AnEp8-hygro were added to the wells of a 96-well cell culture plate and mixed evenly, to obtain a mixture of the spores and the plasmid. The cell culture plate was placed on an ice bath for 15 min, electroporation was carried out subsequently by using the HDEN method using an Etta Biotech X-Porator H1 electroporator, by inserting an electroporator head fitted with a matrix electrode into the mixture of the spores and the plasmid, and energizing, to generate an electric field inside the mixture of the spores and the plasmid. The cell culture plate was placed on the ice bath again for 15 min after electroporation, and subsequently the mixture of the spores and the plasmid was aspirated off, to obtain resting spores of *Aspergillus niger* with introduction of exogenous DNA.

In this example, the parameters for electroporation include: a voltage of 1 V, pulse duration of 2000000 ms, and repeat for 100 times at an interval of 5 ms.

4) Confirmatory Experiment

The aspirated mixture of the spores and the plasmid was coated onto a plate containing YPD solid agar medium with a final concentration of hygromycin B of 200 μg/ml, and cultured at a temperature of 16° C. with 15-50% humidity until single colonies were formed. The colonies were counted and the transformation efficiency was calculated.

At the same time when the above experimental steps were performed, a control group was prepared (as described in Example 1).

When single colonies were formed in the experimental group, DNA was extracted from the single colonies in the experimental group, and the positive clone in this example was confirmed as a successful transformant by the method as described in Example 1.

The volume of the AnEp8-hygro plasmid in this example was 12.4 kb, and 0.1 μg plasmid (about 12.426 fmol plasmid molecules) was used, with which 6×10⁸ non-germinated resting spores of *Aspergillus niger* were electroporated, to produce no less than 6000 positive transformants.

The construction method of the recombinant plasmid AnEp8-hygro in this example was the same as that in Example 1.

Example 3

A method for direct transformation of exogenous DNA into resting spores of *Aspergillus niger* independent of mediators includes the following steps:

1) Culture of *Aspergillus niger* and Collection of Spores

In a 15-cm Petri dish, a solid agar medium (PDA medium) was prepared. *Aspergillus niger* CBS 513.88 was inoculated onto the surface of the solid agar medium and cultured at a temperature of 40° C. with 60-85% humidity for 3 days, to allow *Aspergillus niger* spores to overgrow on the surface of the medium (where the spores appeared dark brown and was easily to visually identified).

Sterilized water was poured onto the surface of the medium, to wash down the *Aspergillus niger* spores off from the surface of the medium (by vibrating, or gently scratching with a sterilized smooth glass spreading rod). The spore suspension was aspirated with a pipette and filtered using sterilized lens paper (or flitted glass filter, filter paper, etc.) to remove the mycelia and retain the spores. The filtered liquid was placed in a centrifuge tube and centrifuged to collect the pelleted resting spores, and the supernatant was discarded. The collected spores were subjected to chromosome staining, to observe and confirm that the chromosomes in the spores are haploid.

2) Pre-Treatment of *Aspergillus niger* Spores

The spore pellets were re-suspended in an electroporation buffer (where the volume of the electroporation buffer added should fill up the centrifuge tube), centrifuged again to collect the spore pellets, and the supernatant was discarded. After repeating the above steps twice, the spores were re-suspended in the electroporation buffer again, and observed under a microscope, to confirm that the spore suspension was free of contamination with mycelia and the spores were non-germinated. When the spores were finally re-suspended in the electroporation buffer, the volume of the electroporation buffer was controlled to maintain a spore concentration in the *Aspergillus niger* spore suspension of 10⁴ spores/ml.

The electroporation buffer consisted of HEPES having a final concentration of 100 mmol/L and mannitol having a final concentration of 5000 mmol/L, and the pH of the electroporation buffer was 7.0.

3) Electroporation of the *Aspergillus niger* Spores by Using HDEN Method

600000 μl of the *Aspergillus niger* spore suspension and 10000 μg of recombinant plasmid AnEp8-hygro were added to wells of a 96-well cell culture plate and mixed evenly, to obtain a mixture of the spores and the plasmid. The cell culture plate was placed on an ice bath for 10 min, electroporation was carried out subsequently by using the HDEN method using an Etta Biotech X-Porator H1 electroporator, by inserting an electroporator head fitted with a matrix electrode into the mixture of the spores and the plasmid, and energizing, to generate an electric field inside the mixture of the spores and the plasmid. The cell culture plate was placed on the ice bath again for 10 min after electroporation, and subsequently the mixture of the spores and the plasmid was aspirated off, to obtain resting spores of *Aspergillus niger* with introduction of exogenous DNA.

In this example, the parameters for electroporation include: a voltage of 6000 V, pulse duration of 2 ms, and repeat for 1 time at an interval of 50000 ms.

4) Confirmatory Experiment

The aspirated mixture of the spores and the plasmid was coated onto a plate containing YPD solid agar medium with a final concentration of hygromycin B of 200 μg/ml, and cultured at a temperature of 40° C. with 60-85% humidity until single colonies were formed. The colonies were counted and the transformation efficiency was calculated.

At the same time when the above experimental steps were performed, a control group was prepared (as described in Example 1).

When single colonies were formed in the experimental group, DNA was extracted from the single colonies in the experimental group, and the positive clone in this example was confirmed as a successful transformant by the method as described in Example 1.

The volume of the AnEp8-hygro plasmid in this example was 12.4 kb, and 10000 μg plasmid (about 1242600 fmol plasmid molecules) was used, with which 6×10⁶ non-germinated resting spores of *Aspergillus niger* were electroporated, to produce no less than 7000 positive transformants.

The construction method of the recombinant plasmid AnEp8-hygro in this example was the same as that in Example 1.

Example 4

In this example, the parameters for electroporation were the same as those in the Example 1 except that the voltage was 30 V, the pulse duration was 1000000 ms, electroporated for 50 times at an interval of 5000 ms, and no less than 6500 positive transformants were produced.

Example 5

In this example, the parameters for electroporation were the same as those in Example 1 except that the voltage was 3000 V, the pulse duration was 100 ms, electroporated for 5 times at an interval of 25000 ms, and no less than 7200 positive transformants were produced.

The method for introducing exogenous DNA into resting spores of *Aspergillus niger* provided in the present invention can be used to introduce not only the recombinant plasmid AnEp8-hygro, but also any other plasmids into resting spores of *Aspergillus niger*.

What is claimed is:

1. A method for direct transformation of exogenous DNA into resting spores of *Aspergillus niger* independent of mediators, comprising steps of:

1) culture of *Aspergillus niger* and collection of spores
    *Aspergillus niger* is inoculated onto a surface of a solid agar medium, and cultured until *Aspergillus niger* spores are overgrown on the surface of the solid agar medium, the *Aspergillus niger* spores are washed off from the surface of the solid agar medium, suspension of the spores is aspirated off and filtered to remove mycelia, and filtrate containing the spores is collected, and centrifuged to collect the pelleted resting spores;

2) pretreatment of *Aspergillus niger* spores
    the spores are re-suspended in an electroporation buffer, and centrifuged to collect the spore pellets, the re-suspension and centrifugation steps are repeated 3-4 times, and the last collected spore pellets are re-suspended in the electroporation buffer, to obtain an *Aspergillus niger* spore suspension with a spore concentration of $10^4$-$10^{11}$ spores/ml,
    in which the electroporation buffer consists of 4-hydroxyethyl piperazine ethanesulfonic acid having a final concentration of 0.01-100 mmol/L and mannitol having a final concentration of 0.5-5000 mmol/L, and the pH of the electroporation buffer is 3.0-9.5; and 3) electroporation of *Aspergillus niger* spores by using high-density distributed electrode network (HDEN) method
    the *Aspergillus niger* spore suspension prepared in the above steps and a plasmid to be transformed are added to wells of a cell culture plate and mixed uniformly, to obtain a mixture of the spores and the plasmid, the cell culture plate is placed on an ice bath for 10-15 min, subsequently electroporation is carried out by using the HDEN method using an Etta Biotech X-Porator H1 electroporator, by inserting an electroporator head fitted with a matrix electrode into the mixture of the spores and the plasmid, and energizing, to generate an electric field inside the mixture of the spores and the plasmid, the cell culture plate is placed on the ice bath again for 10-15 min after the electroporation, and subsequently the mixture of the spores and the plasmid is aspirated off, to obtain resting spores of *Aspergillus niger* with introduction of exogenous DNA, in which ratio of the *Aspergillus niger* spore suspension to the plasmid to be transformed is 6-600000 µl of *Aspergillus niger* spore suspension to 0.1-10000 µg of plasmid to be transformed; and parameters for the electroporation comprise: a voltage of 1-6000 V, pulse duration of 2-2000000 ms, and repeat for 1-100 times at an interval of 5-50000 ms.

2. The method for direct transformation of exogenous DNA into resting spores of *Aspergillus niger* independent of mediators according to claim 1, wherein the solid agar medium in the step 1) is PDA medium, YPD medium, or Czapek-Dox medium.

3. The method for direct transformation of exogenous DNA into resting spores of *Aspergillus niger* independent of mediators according to claim 1, wherein in the step 1), *Aspergillus niger* is cultured at a temperature of 16-40° C. with 15-85% humidity for 3-15 days.

4. The method for direct transformation of exogenous DNA into resting spores of *Aspergillus niger* independent of mediators according to claim 3, wherein in the step 1), *Aspergillus niger* is cultured at a temperature of 30° C. with 50-60% humidity for 5 days.

5. The method for direct transformation of exogenous DNA into resting spores of *Aspergillus niger* independent of mediators according to claim 1, wherein in the step 2), the electroporation buffer consists of 4-hydroxyethyl piperazine ethanesulfonic acid having a final concentration of 1 mmol/L and mannitol having a final concentration of 50 mmol/L, and the pH of the electroporation buffer is 7.0.

6. The method for direct transformation of exogenous DNA into resting spores of *Aspergillus niger* independent of mediators according to claim 1, wherein the *Aspergillus niger* spore suspension in the step 2) is observed under a microscope before electroporation, to confirm that the spore suspension is free of contamination with mycelia and the spores are non-germinated, and subsequently electroporation is carried out.

7. The method for direct transformation of exogenous DNA into resting spores of *Aspergillus niger* independent of mediators according to claim 1, wherein in the step 3), the plasmid to be transformed is recombinant plasmid AnEp8-hygro, and the recombinant plasmid AnEp8-hygro is constructed with a hygromycin B resistance gene and an AnEp8 plasmid.

8. The method for direct transformation of exogenous DNA into resting spores of *Aspergillus niger* independent of mediators according to claim 7, wherein in the step 3), the ratio of the *Aspergillus niger* spore suspension to the recombinant plasmid AnEp8-hygro is 60 µl of *Aspergillus niger* spore suspension to 1 µg of recombinant plasmid AnEp8-hygro.

9. The method for direct transformation of exogenous DNA into resting spores of *Aspergillus niger* independent of mediators according to claim 1, wherein in the step 3), the parameters for the electroporation comprise: a voltage of 400 V, pulse duration of 2000 ms, and repeat for 3 times at an interval of 500 ms.

10. The method for direct transformation of exogenous DNA into resting spores of *Aspergillus niger* independent of mediators according to claim 1, wherein the step 3) further comprises aspirating the mixture of the spores and the plasmid off, coating the mixture onto a plate containing YPD solid agar medium with a final concentration of hygromycin B of 200 µg/ml, culturing the mixture at a temperature of 16-40° C. with 15-85% humidity until single colonies are formed, and counting the single colonies.

* * * * *

SEQUENCE LISTING

<160> NUMBER OF SEQ ID NOS: 5

<210> SEQ ID NO 1
<211> LENGTH: 1026
<212> TYPE: DNA
<213> ORGANISM: Artificial Sequence
<220> FEATURE:
<223> OTHER INFORMATION: Hygromycin B resistance gene

<400> SEQUENCE: 1

```
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg gcccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag gtcgatgcga cgcaatcgt ccgatccgga     900
gccgggactg tcgggcgtac acaaatcgcc cgcagaagcg cggccgtctg gaccgatggc     960
tgtgtagaag tactcgccga tagtggaaac cgacgcccca gcactcgtcc gagggcaaag    1020
gaatag                                                               1026
```

<210> SEQ ID NO 2
<211> LENGTH: 341
<212> TYPE: PRT
<213> ORGANISM: Artificial Sequence
<220> FEATURE:
<223> OTHER INFORMATION: Hygromycin B resistance protein

<400> SEQUENCE: 2

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Pro Ile Cys Ala Ile Ala Asp Pro His Val Tyr
```

```
            145                 150                 155                 160
His Trp Gln Thr Val Met Asp Thr Val Ser Ala Ser Val Ala Gln
                165                 170                 175
Ala Leu Asp Glu Leu Met Leu Trp Ala Glu Asp Cys Pro Glu Val Arg
            180                 185                 190
His Leu Val His Ala Asp Phe Gly Ser Asn Asn Val Leu Thr Asp Asn
            195                 200                 205
Gly Arg Ile Thr Ala Val Ile Asp Trp Ser Gly Ala Met Phe Gly Asp
            210                 215                 220
Ser Gln Tyr Glu Val Ala Asn Ile Phe Phe Trp Arg Pro Trp Leu Ala
225                 230                 235                 240
Cys Met Glu Gln Gln Thr Arg Tyr Phe Glu Arg Arg His Pro Glu Leu
                245                 250                 255
Ala Gly Ser Pro Arg Leu Arg Ala Tyr Met Leu Arg Ile Gly Leu Asp
            260                 265                 270
Gln Leu Tyr Gln Ser Leu Val Asp Gly Asn Phe Asp Asp Ala Ala Trp
            275                 280                 285
Ala Gln Gly Arg Cys Asp Ala Ile Val Arg Ser Gly Ala Gly Thr Val
            290                 295                 300
Gly Arg Thr Gln Ile Ala Arg Arg Ser Ala Ala Val Trp Thr Asp Gly
305                 310                 315                 320
Cys Val Glu Val Leu Ala Asp Ser Gly Asn Arg Arg Pro Ser Thr Arg
                325                 330                 335
Pro Arg Ala Leu Glu
            340

<210> SEQ ID NO 3
<211> LENGTH: 6638
<212> TYPE: DNA
<213> ORGANISM: Artificial Sequence
<220> FEATURE:
<223> OTHER INFORMATION: AnEp8 plasmid

<400> SEQUENCE: 3
atgtcttaga aaaataaaca aatagggggtt ccgcgcacat ttccccgaaa agtgccacct      60
gctaagaaac cattattatc atgacattaa cctataaaaa taggcgtatc acgaggccct     120
ttcgtctcgc gcgtttcggt gatgacggtg aaaacctctg acacatgcag ctcccggaga     180
cggtcacagc ttgtctgtaa gcggatgccg ggagcagaca gccccgtcag ggcgcgtcag     240
cgggtgttgg cgggtgtcgg gctggctta actatgcggc atcagagcag attgtactga     300
gagtgcacca tatgcggtgt gaaataccgc acagatgcgt aaggagaaaa taccgcatca     360
ggcgccattc gccattcagg ctgcgcaact gttgggaagg gcgatcggtg cgggcctctt     420
cgctattacg ccagctggcg aaagggggat gtgctgcaag gcgattaagt tgggtaacgc     480
cagggttttc ccagtcacga cgttgtaaaa cgacggccag tgccaagctt gcatgcctgc     540
aggtccgcga atattccgga gatcctgatc atccgtgaga atgaagagga agttgggttt     600
gcgtgcagag accgatggct cctcatccag cagtacctgc tgctgcacag cgagggcatc     660
gcatcccacg aatagggcca acaaagccgg caagaacatc atgatgggag cgacaattcc     720
gtatcaatct ccccttgcacg atgttggttg tcactcaccg acactccgtc accaagatca     780
ctattaaaac aagagtgagt tcaaggttgc gatcaagata gcgattgcgc agcaacggca     840
cgggataacg ccatagctct gatggagccg atcagaccag taggtaaact agtcagtcag     900
cgttggactg gagctgcaga gagagttgaa cctggacgcc gcgcaaaaag caaagacgcg     960
```

```
cctcgtgggc ggtggatcaa tgatcggatt tagtggcaga tggcatcaca ggcggccaat    1020
gaccaccggg ccaactggcc ccgacattcc agcaatactg cctaattgac tccaccatgc    1080
atctcggcta ttattgaact gggtttgatg gatgggacc ctcttggaat tgtcaaagat     1140
tttgaagcga agacgatcta ttggacggta gagatatact cttgatttag tcgttgggag    1200 gccctgggg aaagcaatga tggggaatgt tgctgctcca ctgtggacct cggctatgga    1260
attacgtgct tggatctaag atgagctcat ggctatgcat tgaatgacag tgatatcagc    1320
agagcaagca gagaaggatg gaatgctaat tttctagtgc tttgtgcaag ggtaaatcag    1380
ggactgtctg tctggtcttc tacacgaagg aagaccatg gctttcacgg tgtctgtatt     1440
tccggatatc ctcaattccg tcggtcgatt acaatcacat gacttggctt ccatttcact    1500
actattatgc acaccacta catacatgat catataacca attgccctca tccccatcct     1560
ttaactatag cgaaatggat tgattgtcta ccgccaggtg tcagtcaccg tcgcggtcgg    1620
gccggccggc gcgccgttta aacttaatta agctagctga ttgatctcta ctgaaccggg    1680
ggggaagaca gaagagaagg gattgatgaa gatgggagaa agaatggagg gagagaaggg    1740
aggagaagag ggagagataa tagggaagga aaagacgggg ccggtgagcg agagaagaga    1800
gagatggtgg actagaggag gggtgcccgg gaaggaaaaa tgttggcggc ggtgattggc    1860
tggatcggcc cttttggtg ggattcctgc tttgggacgc ttttttctgt cggtcggttc     1920
cccgcgggtt gagagctggc ttgttagttg tgcctccagc tacggagtag ttacaatcac    1980
acttcccatc gcctacataa ttcccattat taatgacttt ttctccccc cggcactatc     2040 gctgggtatc aaaactcaat tatttgctgg gtgatccacc tttcactgct ttgctactat    2100
tctttgatcg tagatacacc tgctgcctcc gtccgctctt ttcactggtc agccaagggt    2160
ttccgcccag cgatcagcag catttgtcca ctacatcctc aggcaccttc cctccgcgca    2220
tctcaggcat tcatacgccg catgcaataa taattggttg ggaagaccaa aagcaattca    2280
cgcccaagcc acaatcagac acccacacaa cattctgcga agtatctggc aggaccacat    2340 gatacccctct cactctgtcc agttgacccc acatcgtcgc ggatccattc tctcctagcg    2400
aggtggattt ggatgctttg tcggtgctga atttttctcct cgcaaaaaag cccaatgccc    2460
ttcgcaagaa ctatttccct gactccatcg gaacccataa ggctgaattt tgctctgctc    2520
ggacggaccc agttgccagt tatggagaag ctgtctccct ttttattttt attttatttt    2580 attttttgt ccagtgggta attaatcata gtaatgagga cgagactctg gccagtagac     2640
agggacccta agtaagtact cggaggtttt ctcttccatt tacgcgtggt atatgccctt    2700
cattaatatg gctagtacta ttatgatccc catatatcct tttccgaggc cagacacgtc    2760
catcattcat ctcataaggc taagttcctg accgtccgga cccctccgcc aatggcatca    2820
gatgtgggac gtccccttt agtcaatacc gttacacatt tccactcaca ctcaaagtcc    2880 aactctttt tcgtaagctt tccagccttc ctcccggtac ctctgaaccg cctcgactgg    2940
atcgtccgcc ttatagatgc ccctacccgc aatgataaag tccgcacctc gcccaaccgc    3000
cgacccaggt gtctgatact gctgcccag cttatccccc ttatccgaca gattcacccc     3060
agtcgtaaag acgacaaaat cctcgctctc ctctttctgt tcgggcagca cctcactcaa    3120 cgccttgta ctcacgaatc ccatcacaaa ccccttatac ttccgcgcgt actcaaccga     3180
gcgtgccgtg tactccctg tcgcaagaga tccttactc gtcatctcgg caagaatcag     3240
gagacctcgt tgattcgcgt ctttaaagtc aggagacttg gttgtctgtg cgagggcctc    3300
```

```
gacgatccct tcgcccggca ggatggcgca gttgatgatg tgtgcccatt cggagatgcg    3360
gagagcgcca ccgtggtact gcttttgcac ggtgttgccg atgtcgatga acttgcggtc    3420
ctcaaagatg aggaagttgt gctttgtcgc gagggattgg agcgaggaaa gggtcgacgg    3480
ggtgagatcg gtgaggatgt cgatgtgggt tttcagaact gcgatatagg ggcctaggcc    3540
tgtactcact acgcatcagc tatttgttat cctggagggg cattggtgca ggatgtacgg    3600
tcagcaagat cgaggagctc ggcggaagta gtaacgtctg cggagacggt gacgttggtt    3660
ttcttctcct cggcgatgga gaagagttta gatgttaaag ggttgggatg gttggttgcg    3720
cgaattgcgt aggggaggtg ggacttcgaa gacatgatgg cggttctcca atgattgaat    3780
tgggctggat taaactgaca atttgaagct ggaagtggga tggctgtata acgaaaactc    3840
accccgctgc ggtggaattt ttgctccggc ccgataagat aggcgcagac ctatctccac    3900
tatcacgaat ataggtcacg aacccgacta tcattcaaac agaccacatt ttatcaactc    3960
tcccctctgt gctaagatgt cgactacatt tacatcaaat cctttgcaac accaaatgcg    4020
ctcaatcccc aaagacccgc ttgcgcaagc aagtacagcg aaccattgta cctgccggtg    4080
ccgttcggct tgtcgctata aatatagccc agcatgtaga gggtgcggag aacaacccag    4140
gccgctccta agcccgctgc tgcctctggg tacttgacgc ctgccaccag gatagagagc    4200
attgtctgcg gcgcgttctc gaggaagttg cgcggccgca agcttatttt ttgtatactg    4260
ttttgtgata gcacgaagtt tttccacggt atcttgttaa aaatatatat ttgtggcggg    4320
cttacctaca tcaaattaat aagagactaa ttataaacta aacacacaag caagctactt    4380
tagggtaaaa gtttataaat gcttttgacg tataaacgtt gcttgtattt attattacaa    4440
ttaaaggtgg atagaaaacc tagagactag ttagaaacta atctcaggtt gcgttaaac    4500
taaatcagag cccgagaggt taacagaacc tagaagggga ctagatatcc gggtagggaa    4560
acaaaaaaaa aaaacaagac agccacatat tagggagact agttagaagc tagttccagg    4620
actaggaaaa taaagacaa tgataccaca gtcagttga caactagata gattctagat    4680
tgaggccaaa gtctctgaga tccaggttag ttgcaactaa tactagttag tatctagtct    4740
cctataactc tgaagctaga ataacttact actattatcc tcaccactgt tcagctgcgc    4800
aaacggagtg attgcaaggt gttcagagac tagttattga ctagtcagtg actagcaata    4860
actaacaagg tattaaccta ccatgtctgc catcaccctg cacttcctcg ggctcagcag    4920
ccttttcctc ctcatttttca tgctcatttt ccttgtttaa gactgtgact agtcaaagac    4980
tagtccagaa ccacaaagga gaaatgtctt accactttct tcattgcttg tctcttttgc    5040
attatccatg tctgcaacta gttagagtct agttagtgac tagtccgacg aggacttgct    5100
tgtctccgga ttgttggagg aactctccag ggcctcaaga tccacaacag agccttctag    5160
aagactggtc aataactagt tggtctttgt ctgagtctga cttacgaggt tgcatactcg    5220
ctcccttttgc ctcgtcaatc gatgagaaaa agcgccaaaa ctcgcaatat ggctttgaac    5280
cacacggtgc tgagactagt tagaatctag tcccaaacta gcttggatag cttaccttttg    5340
cccttttgcgt tgcgacaggt cttgcagggt atggttcctt tctcaccagc tgatttagct    5400
gccttgctac cctcacggcg gatctgcata aagagtggct agaggttata aattagcact    5460
gatcctaggt acggggctga atgtaacttg cctttccttt ctcatcgcgc ggcaagacag    5520
gcttgctcaa attcctacca gtcacagggg tatgcacggc gtacggacca cttgaactag    5580
tcacagatta gttagcaact agtctgcatt gaatggctgt acttacgggc cctcgccatt    5640
gtcctgatca tttccagctt caccctcgtt gctgcaaagt agttagtgac tagtcaagga    5700
```

```
ctagttgaaa tgggagaaga aactcacgaa ttctcgacac ccttagtatt gtggtccttg    5760
gacttggtgc tgctatatat tagctaatac actagttaga ctcacagaaa cttacgcagc    5820
tcgcttgcgc ttcttggtag gagtcggggt tgggagaaca gtgccttcaa acaagccttc    5880
ataccatgct acttgactag tcagggacta gtcaccaagt aatctagata ggacttgcct    5940
ttggcctcca tcagttcctt catagtggga ggtccattgt gcaatgtaaa ctccatgccg    6000
tgggagttct tgtccttcaa gtgcttgacc aatatgtttc tgttggcaga gggaacctgt    6060
caactagtta ataactagtc agaaactagt atagcagtag actcactgta cgcttgaggc    6120
atcccttcac tcgcagtag acttcatatg gatggatatc aggcacgcca ttgtcgtcct    6180
gtggactagt cagtaactag gcttaaagct agtcgggtcg gcttactatc ttgaaatccg    6240
gcagcgtaag ctccccgtcc ttaactgcct cgagatagtg acagtactct ggggactttc    6300
ggagatcgtt atcgcgaatg ctcggcatac taatcgttga ctagtcttgg actagtcccg    6360
agcaaaaagg attggaggag gaggaggaag gtgagagtga gacaaagagc gaaataagag    6420
cttcaaaggc tatctctaag cagtatgaag gttaagtatc tagttcttga ctagatttaa    6480
aagagatttc gactagttat gtacctggag tttggatata ggaatgtgtt gtggtaacga    6540
aatgtaaggg ggaggaaaga aaaagtcggt caagaggtaa ctctaagtcg gccattcctt    6600
tttgggaggc gctaaccata aacggcatgg cggcatgg                            6638
```

```
<210> SEQ ID NO 4
<211> LENGTH: 33
<212> TYPE: DNA
<213> ORGANISM: Artificial Sequence
<220> FEATURE:
<223> OTHER INFORMATION: Forward primer for hygromycin B resistance gene

<400> SEQUENCE: 4
cattagctag catgaaaaag cctgaactca ccg                                  33

<210> SEQ ID NO 5
<211> LENGTH: 29
<212> TYPE: DNA
<213> ORGANISM: Artificial Sequence
<220> FEATURE:
<223> OTHER INFORMATION: Reverse primer for hygromycin B resistance gene

<400> SEQUENCE: 5
tctggcgcgc cctattcctt tgccctcgg                                       29
```